United States Patent
Nilsson et al.

(10) Patent No.: US 9,844,487 B2
(45) Date of Patent: Dec. 19, 2017

(54) DRIVING CONTROL OF A RECIPROCATING CPR APPARATUS

(75) Inventors: Anders Nilsson, Åkarp (SE); Peter Sebelius, Malmö (SE)

(73) Assignee: Physio-Control, Inc., Redmond, WA (US)

( * ) Notice: Subject to any disclaimer, the term of this patent is extended or adjusted under 35 U.S.C. 154(b) by 998 days.

(21) Appl. No.: 13/549,164

(22) Filed: Jul. 13, 2012

(65) Prior Publication Data

US 2012/0283608 A1    Nov. 8, 2012

Related U.S. Application Data

(62) Division of application No. 12/523,082, filed as application No. PCT/SE2008/000022 on Jan. 14, 2008, now abandoned.

(30) Foreign Application Priority Data

Jan. 18, 2007 (SE) ...................................... 0700094

(51) Int. Cl.
   *A61H 31/00* (2006.01)
   *A61M 16/00* (2006.01)

(52) U.S. Cl.
   CPC ... *A61H 31/006* (2013.01); *A61H 2201/1246* (2013.01); *A61H 2201/1664* (2013.01); *A61H 2201/5007* (2013.01); *A61H 2201/5064* (2013.01); *A61H 2201/5066* (2013.01); *A61H 2201/5092* (2013.01); *A61M 16/00* (2013.01)

(58) Field of Classification Search
   CPC .... A61H 31/00; A61H 31/004; A61H 31/005; A61H 31/006; A61H 2201/1238; A61H 2201/1246; A61H 2201/1619; A61H 2201/5056; A61H 2201/5064; A61H 2201/5066; F04B 2201/0201; F04B 2203/0903; F15B 11/046; F15B 15/1414; F15B 15/2861
   USPC ............................................. 74/574.4, 574.1
   See application file for complete search history.

(56) References Cited

U.S. PATENT DOCUMENTS

| | | |
|---|---|---|
| 3,209,747 A | 10/1965 | Guentner |
| 3,277,887 A | 10/1966 | Thomas |
| 3,364,924 A | 1/1968 | Barkalow |

(Continued)

FOREIGN PATENT DOCUMENTS

WO    02091905 A2    11/2002

OTHER PUBLICATIONS

International Search Report, dated Jun. 9, 2008, 4 pages, PCT/SE2008/000022, Swedish Patent Office, Stockholm, Sweden.

(Continued)

*Primary Examiner* — Michael Tsai
(74) *Attorney, Agent, or Firm* — Lane Powell, PC

(57) ABSTRACT

A method of controlling the amount of compressed gas used for driving a reciprocating apparatus for cardio-pulmonary resuscitation (CPR) comprising a valve means for controlling the provision of driving gas comprises operation of the valve means during the compression phase to stop provision of driving gas, which operation is separated in time from the venting of the driving gas from the apparatus at the end of the compression phase. Also disclosed are; a CPR apparatus operated by the method; a method of compression depth sensing.

11 Claims, 14 Drawing Sheets

(56) References Cited

U.S. PATENT DOCUMENTS

| | | | |
|---|---|---|---|
| 3,779,672 A * | 12/1973 | Schroeder | F04B 27/02 417/493 |
| 4,343,597 A * | 8/1982 | Brown | 417/417 |
| 4,471,656 A | 9/1984 | Sanders et al. | |
| 4,726,366 A * | 2/1988 | Apple et al. | 128/204.21 |
| 4,905,520 A * | 3/1990 | Nehrlich | G01L 9/14 338/32 H |
| 6,030,353 A | 2/2000 | Van Brunt | |
| 6,155,257 A * | 12/2000 | Lurie et al. | 128/204.23 |
| 6,171,267 B1 | 1/2001 | Baldwin, II | |
| 6,215,299 B1 * | 4/2001 | Reynolds | G01D 5/145 324/207.2 |
| 6,397,843 B1 * | 6/2002 | Tien-Tsai | 128/204.18 |
| 6,652,039 B1 * | 11/2003 | Shull | B60T 8/404 303/113.2 |
| 6,919,719 B2 * | 7/2005 | Reininger | F15B 15/2807 324/207.12 |
| 7,118,542 B2 | 10/2006 | Palazzolo et al. | |
| 7,226,427 B2 | 6/2007 | Steen | |
| 7,517,325 B2 | 4/2009 | Halperin | |
| 8,007,451 B2 * | 8/2011 | Havardsholm et al. | 601/41 |
| 2003/0181834 A1 | 9/2003 | Sebelius et al. | |
| 2004/0230140 A1 | 11/2004 | Steen | |
| 2004/0263155 A1 * | 12/2004 | Schroeder | G01D 5/2515 324/207.12 |
| 2005/0058977 A1 | 3/2005 | Cantrell et al. | |
| 2006/0059995 A1 * | 3/2006 | Gustafson | G01L 9/14 73/736 |
| 2006/0087313 A1 | 4/2006 | Revankar et al. | |
| 2006/0196354 A1 * | 9/2006 | Garcia | F15B 15/1414 92/165 PR |
| 2007/0270724 A1 | 11/2007 | Havardsholm et al. | |
| 2007/0276300 A1 | 11/2007 | Olson et al. | |
| 2011/0120300 A1 * | 5/2011 | Fletcher | F15B 15/2861 92/5 R |

OTHER PUBLICATIONS

Written Opinion, dated Jun. 9, 2008, 5 pages, PCT/SE2008/000022, Swedish Patent Office, Stockholm, Sweden.
European Search Report for EP Application No. 13155766.2, dated May 8, 2013, 6 pages.

* cited by examiner

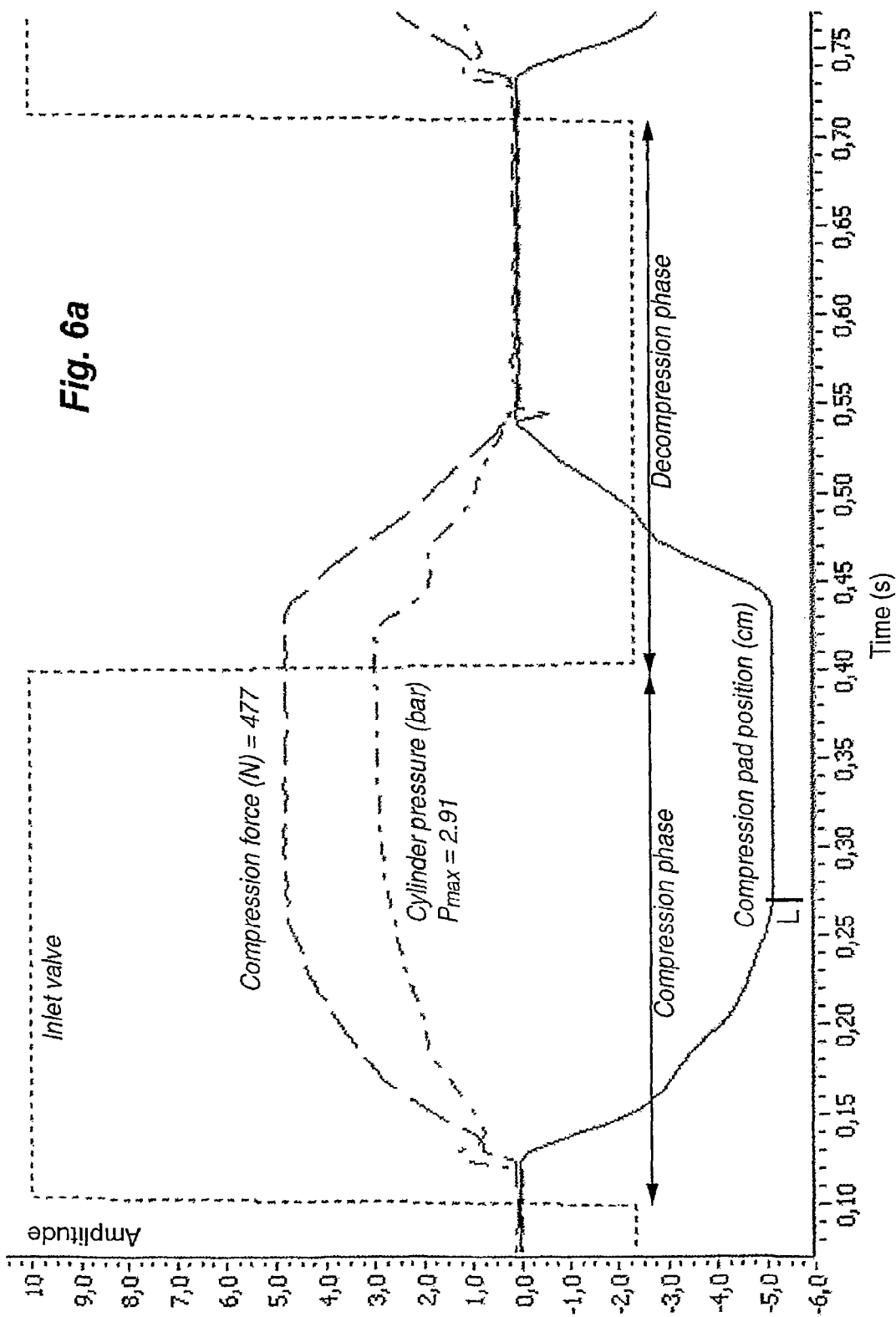

US 9,844,487 B2

DRIVING CONTROL OF A RECIPROCATING CPR APPARATUS

RELATED APPLICATIONS

This application is a division of U.S. patent application Ser. No. 12/523,082, filed Aug. 13, 2009 and currently pending, which is a national stage entry of International patent application no. PCT/SE2008/000022, filed Jan. 14, 2008, which claims the benefit of Swedish Application No. 0700094-6, filed Jan. 18, 2007.

FIELD OF THE INVENTION

The present invention relates to a method of sensing the chest compression depth in a reciprocating apparatus for cardio-pulmonary resuscitation (CPR) driven by a compressed gas, a method of controlling the amount of compressed gas used for driving a reciprocating apparatus for cardiopulmonary resuscitation (CPR), and a correspondingly operated reciprocating CPR apparatus.

BACKGROUND OF THE INVENTION

In cardio-pulmonary resuscitation (CPR) repeated compressions are administered by hand or by apparatus to the chest of the person being resuscitated to maintain circulation and oxygenation of blood. Concomitant with the compressions electrical shocks are provided to the patient to make the heart beat again. Gas-driven reciprocating CPR apparatus have been known in the art and used in practice for a long time; see, for instance, U.S. Pat. No. 3,209,747 (Guentner) and U.S. Pat. No. 3,277,887 (Thomas). Providing compressions of correct depth is an important factor for success of the method.

In the following "Compression Depth" signifies the maximum sternal deflection during a compression/decompression cycle. An appropriate Compression Depth for adult persons corresponds to a sternal deflection of 20%; the compression depth for a chest with an anterior-posterior diameter of 25 cm thus is 5 cm. In contrast "compression depth" in the following refers to a sternal deflection during a compression/decompression cycle smaller than the maximum deflection or to sternal deflection in general.

Shallow compressions may be insufficient to restore circulation and oxygenation while compressions that are too deep may damage the ribs and the soft tissues of the chest. There is thus an optimal Compression Depth or a narrow range of optimal Compression Depths. Administration of compressions of optimal Compression Depth may be controlled by administering compressions of a given force. Alternatively, a desired Compression Depth may be set by an operator; it may be optionally changed during resuscitation. Alternatively, the Compression Depth in a CPR apparatus can be set by limiting the stroke of the piston in the apparatus to the average optimal Compression Depth for an adult person. A given compression force results in a compression to a Compression Depth at which the compression force is balanced by the resistive force of the chest tissues. Since even adult persons differ in their chest anatomy a given compression force may result in compression of varying depth in a group of persons. Therefore the direct determination of Compression Depth during cardiopulmonary resuscitation and its use for control of the apparatus by which the compressions are administered is desirable.

The determination of compression depths during cardiopulmonary resuscitation is known in the art. A corresponding device and a method based on accelerometer measurements disclosed in U.S. Pat. No. 7,118,542. An accelerometer-based compression monitor is placed on the patient's sternum, the arm of a rescuer administrating manual heart compressions or on a compression-administrating part of an automatic CPR device. The chest is then compressed. The accelerometer signal is integrated and fed to a processor, which calculates the compression depth from the signal by use of complex algorithms. The accelerometer is electrically connected to the processor.

In the administration of repeated compressions in cardiopulmonary resuscitation the use of apparatus based on a reciprocating piston provided with a chest compression pad and mounted in a cylinder is known. The piston is driven by a compressed gas. An apparatus of this kind dedicated for use by off-hospital medical emergency teams is disclosed in US 2003/0181834. The Compression Depth administered with such an apparatus is limited by physical means comprised by the apparatus and set from start to from about 40 mm to about 50 mm for an adult person.

A problem with CPR apparatus driven by a compressed gas is limited gas supply, since the apparatus may be used for an hour or more to provide compressions to the patient during transport to a hospital by, for instance, an ambulance.

OBJECTS OF THE INVENTION

It is an object of the invention to provide a method of determining the Compression Depth in cardiopulmonary resuscitation and, optionally, a compression depth, in particular as administered by a reciprocating apparatus for cardio-pulmonary resuscitation driven by a compressed gas, in particular by a compressed breathing gas, in which the Compression Depth is not limited by physical means comprised by the apparatus.

It is another object of the invention to provide such determination over one or multiple compression cycles.

It is further object of the invention to provide a corresponding means.

Still another object of the invention to provide a method of optimizing the use of compressed breathing gas for driving the apparatus based on the determination of the Compression Depth and/or a compression depth.

An additional object of the invention is to provide a reciprocating apparatus for cardio-pulmonary resuscitation driven by a compressed gas, provided with said means and control means for optimizing the use of driving gas.

Still further objects of the invention will become apparent from the study of the following summary of the invention, the description of preferred embodiments thereof illustrated in a drawing, and the appended claims.

SUMMARY OF THE INVENTION

According to the present invention is disclosed a method of sensing the Compression Depth and/or a compression depth in a reciprocating apparatus for cardio-pulmonary resuscitation (CPR) driven by a compressed gas and comprising a reciprocating part and a non-reciprocating part, the method comprising arranging a sensor mounted on the non-reciprocating part capable of sensing a signal emanating from the reciprocating part at a selected position thereof; transmitting the signal to a microprocessor unit that records its arrival time.

It is preferred for the non-reciprocating part to comprise a cylindrical housing having a top wall, a bottom wall and a side wall, and for the reciprocating part to comprise a piston disposed in the housing so as to allow displacement thereof by a compressed gas adduced to an upper compartment in the housing defined by the top wall, a portion of the side wall, and the piston. Additionally, displacement in the opposite direction may be effected by adducing a compressed gas to a lower compartment in the housing defined by the bottom wall, a portion of the side wall, and the piston. When administering CPR compressions to a recumbent patient the housing is disposed above the patient's chest. A compression pad fixed at one end of a plunger or piston rod extending through a bore in the bottom wall, the other end of which is fixed to the piston, is placed on the sternal region of the chest. In this application indications of direction and position, such as "upper", "upwards", "top" and "lower", "bottom", "downwards", are governed by this disposition of the CPR apparatus in respect of the patient.

The cylinder walls and the piston are preferably of a diamagnetic material, in particular an organic polymer material, for instance polystyrene or polyester, in particular polyamide, possibly reinforced with organic or inorganic fibre.

While contactless sensing is preferred, sensing by contact is comprised by the method of the invention. In contactless sensing it is preferred to sweep one or several magnetic or radiation sensors mounted at the non-reciprocating part with a magnetic field or radiation, respectively, emanating from a corresponding field or radiation source mounted at or deflected or reflected by the reciprocating part, thereby giving rise to an electric signal in a swept sensor. The radiation source is one emitting radiation in the UV, visible or IR range of the spectrum. Alternatively the radiation source is an ultrasound source, and the radiation detector is an ultrasound detector.

It is preferred to keep the Compression Depth of the apparatus constant by physical means, and for a contact sensor to be activated at the moment when the reciprocating part reaches the Compression Depth.

It is preferred for the one or several magnetic sensors to be disposed on the outer face of the side wall, in particular in a line or array extending in an axial direction. In this application an axial direction is one extending in parallel with the axis of the cylindrical housing. The magnetic field source is a permanent ring or rod magnet mounted on or in the piston. In such case the piston should be of a diamagnetic material, such as glass or carbon fibre reinforced polyamide. Particularly suited materials for the ring or rod magnet are Al—Ni, neodymium and samarium cobalt. Preferred magnetic sensors comprise Hall-effect elements such as unipolar, bipolar, and omnipolar Hall-effect digital switches.

It is preferred for the radiation source to be disposed at the inner face of the bottom, its radiation being directed at the bottom face of the piston, which is diffusely or mirroring reflective or comprises a diffusely or mirroring reflective material capable of reflecting or mirroring, respectively, of more than 20%, preferably more than 50%, even more preferred more than 80% or the incident radiation. It is preferred for the one or several radiation sensors to be disposed at the inner face of the bottom. If there are two or more radiation sensors they are preferably disposed in a line or an array, such as a line or array extending in a radial direction. In this application "radial direction" is a direction extending radially from the centre of the piston. The detection of the position of the piston may be based on total reflected radiation detected by the one or several radiation sensors or by detection of reflected radiation by two or more radiation sensors so disposed that each sensor receives a maximum of reflected radiation from a position of the piston that is different from that from which an adjacent sensor receives a maximum of reflected radiation. It is preferred for the radiation source to be a source of visible, UV or IR light. A preferred source of radiation is a light-emitting diode (LED). Preferred optical sensors are sensors capable of detecting the radiation emitted from the radiation source, in particular sensors capable of detecting radiation reflected by the reflective material, such as photodiodes and phototransistors.

The contactless method of the invention and the corresponding means thus allow to monitor the position of the compression pad over time, such as over one or several compression cycles. In an reciprocating CPR apparatus with a pre-set compression depth by use of a physical Compression Depth limiter it is possible to monitor the moment at which, or whether, the Compression Depth is reached by an electrical contact mounted at or in proximity of the limiter, which is actuated by the piston so as to close or open an electrical circuit, thereby producing an electrical recordable signal.

According to an important aspect of the invention, which is explained below in detail, monitoring the Compression Depth and/or a compression depth can be used to optimize, that is, to minimize the consumption of driving gas in a reciprocating CPR apparatus of the aforementioned kind. This allows to substantially reduce the consumption of driving gas by CPR apparatus.

The initial resistance of the chest of adult persons to a compression of 50 mm is in the order of about 300 N to 400 N. To provide desired rapid compressions at a rate of from about 60 min.sup.-1 to 120 min.sup.-1 and more, a gas-driven reciprocating CPR apparatus has to be driven with a pressure that is substantially higher than the pressure required to just overcome this resistance. This pressure is, of course, also dependent on the area of the piston in the CPR apparatus. From a standpoint of driving gas supply economy, a suitable driving gas pressure is from about 2.5 to 4 bar, preferably about 3 bar. A suitable piston area for a driving gas pressure of 3 bar is about 20 cm.sup.2. This driving gas pressure is however only needed during a short period from the start of providing chest compressions to the patient, such as for a period of one or two minutes. During this period the resistance of the chest decreases by about 50 percent. In consequence, a lower pressure is required to administer compressions of same depth during the following steady-stated period in which the resistance of the chest does not change.

In a compression cycle of the steady-state period the provision of driving gas to the CPR apparatus is only required during a portion of the compression phase, in particular over a period extending from the onset of the compression phase to shortly before the compression depth is reached, such as from 10 to 50 milliseconds, more preferred from 20 to 40 milliseconds, most preferred about 30 milliseconds before the Compression Depth is reached. Thereby the consumption of driving gas can be substantially reduced, such as by 40 percent and even up to 50 percent. By definition the onset of the compression phase is determined by the opening of the valve controlling the supply of gas to the cylinder. The cylinder starts its downward movement shortly thereafter. The end of the compression phase and the start of the decompression phase is determined by the opening of a valve for venting the used driving gas from the upper compartment. At the same time, the piston can be returned to its starting position by adducing compressed driving gas to the lower compartment. Thereby the compression pad, which abuts the breast of the patient and carries a circumferential soft sealing rim or is provided with an adhesive, brings the patient's breast back to its original position. In the absence of such breast returning means the passive return by the chest's resilience is much slower and not its original position.

According to the present invention is also disclosed a method of controlling the amount of compressed gas, such as compressed air, used for driving a CPR apparatus of the aforementioned kind over a reciprocating cycle, comprising a method of determining the compression Depth and/or a compression depth, including determining the moment at which the Compression Depth and/or a compression depth is reached; that moment is preferably determined by sensor means mounted at a non-reciprocating part of the apparatus sensing radiation reflected from a reciprocating part of the apparatus or a magnetic field moving with a reciprocating part of the apparatus.

The method of controlling the amount of compressed gas used for driving a CPR apparatus is based on the insight that the supply of compressed gas to the compartment of the cylinder in which the gas expands and drives the piston against the resistance of the patient's chest tissues is a dynamic process. In this process equilibrium between the gas pressure in the reservoir, in which partially decompressed gas from the gas cylinder is stored at an about constant pressure, and said compartment is not established. To safeguard the working of the apparatus within specifications such as compression rate and waveform the pressure of the gas fed to the compartment must be substantially higher than the pressure that is needed to displace the piston to the Compression Depth in a situation of equilibrium. According to the invention the amount of gas used required for compression to the Compression Depth can be substantially reduced by stopping the supply of gas to the compartment at the moment when the compression depth is reached or, preferably, shortly before that moment.

In the method of controlling the amount of compressed gas the moment at which the Compression Depth and/or a compression depth is reached, which moment may have been determined in (a) preceding reciprocating cycle(s), is used for positional control of valve means through which the compressed gas is adduced to the upper compartment in the housing. At the moment at which a selected position, in particular the Compression Depth, is reached during a reciprocating cycle, that is, when the piston including a compression pad mounted to the piston is in its extreme downward position, or at a prior point in time during that cycle, the microprocessor means operates the valve means, for instance a solenoid valve control unit comprising one or several solenoid valves, so as to stop the flow of compressed gas to the upper compartment of the housing. It is preferred for the prior point in time to be from 0 to 50 milliseconds prior, in particular from 0 to 30 milliseconds prior, most preferred about 10 to 15 milliseconds prior to the moment at which the compression depth is reached. In addition and independently thereof it is preferred for the valve means to stop providing driving gas to the upper compartment after at point in time when the pressure of the gas in the upper compartment is from 30 to 70 percent of the pressure of the driving gas, more preferred from 40 to 60 percent, most preferred about 50 percent. A preferred driving gas pressure is from 2.5 to 4 bar, more preferred about 3 bar. It is also preferred for the portion of the compression phase during which the valve means allow driving gas to enter the upper compartment to extend from the start of the compression phase until a point in time when from 25 percent to 40 percent of the length of the compression phase has passed.

In particular, the method of controlling the amount of compressed gas used for driving a reciprocating apparatus for cardiopulmonary resuscitation (CPR) comprising a valve means for controlling the provision of driving gas to a reciprocating part of the apparatus and for venting of the used driving gas from the apparatus, comprises: (a) operating the valve means at the start of a compression/decompression cycle to provide driving gas; (b) operating the valve means during the compression phase to stop provision of driving gas; (c) operating the valve means at the end of the compression phase to vent the driving gas from the apparatus. Step (b) is preferably initiated at a point in time when the pressure of the provided driving gas is from 30 percent to 70 percent of the pressure of the driving gas, more preferred from 40 percent to 60 percent of the pressure of the driving gas, most preferred about 50 percent. It is also preferred for step (b) to be initiated at a point in time which is at from 25 percent to 40 percent of the length of the compression phase, in particular at a point in time before the moment at which a compression pad of the reciprocating part has reached the Compression Depth.

According to the present invention is additionally provided a method of controlling the amount of compressed gas, such as compressed breathing gas, used for driving a CPR apparatus of the aforementioned kind but in which the piston stroke, that is, the Compression Depth, is mechanically controlled. Mechanical control of the Compression Depth is obtained by mechanically stopping the piston at a desired length of stroke by, for instance, the bottom of the cylinder or a circumferential flange arranged on the inner face of the cylinder between the piston and the bottom. The method of control comprises determining the moment at which the Compression Depth is reached during a reciprocating cycle, which moment may have been determined in (a) preceding reciprocating cycle(s). Alternatively and/or additionally, the method of control comprises determining the moment at which a compression depth is reached during a reciprocating cycle, which moment may have been determined in (a) preceding reciprocating cycle(s). The means for determining the moment at which the Compression Depth and/or a compression depth is reached include those described above but can also, for instance, comprise a simple mechanically operated electric switch that is switched by impact of, for instance, the piston at the moment or close to the moment at which the piston is stopped by the stopping means. The method is used for positional control of valve means through which the compressed gas passes into the upper compartment in the housing. At the moment when the Compression Depth is reached (that is, when the piston is in its extreme downward position) or slightly prior to that moment, the microprocessor means operates the valve means, for instance a solenoid valve control unit comprising one or several solenoid valves, so as to stop the flow of compressed gas to the upper compartment of the housing. "Slightly prior to that moment" signifies from 0 to 50 milliseconds, in particular from 0 to 30 milliseconds, most preferred about 10 to 15 milliseconds prior to the moment at which the piston reaches the compression depth. The stroke length of the CPR apparatus in which the compression depth is mechanically controlled may be fixed or can be set prior to or even during CPR.

According to the present invention is disclosed a CPR apparatus comprising a housing and a reciprocating piston mounted in the housing driven by a pressurized gas, in particular a pressurized breathing gas such as air. The apparatus further comprises a means for sensing the compression depth, in particular a means for contactless sensing.

A compression pad is mounted to the piston via a plunger and is placed on the chest of a patient above the sternum. The reciprocating movement of the piston is so transferred to the pad, and it is by the pad that the patient's chest is compressed to the Compression Depth. The frequency of compression can be varied but is typically in the order of 60 to 120 cycles per minute.

It is preferred for the sensing means to comprise a source of radiation or of a magnetic field and one or several radiation or magnetic field sensors, respectively. It is preferred for the source of radiation and for the optical sensor(s) to be mounted at a non-reciprocating part of the apparatus and for the sensing means to comprise a reflective area disposed on a top or bottom face of the piston. It is preferred for the source of magnetic field to be mounted at a reciprocating part of the apparatus, in particular the piston, and for the field detection source to be mounted at a non-reciprocating part of the apparatus, in particular an inner face of the bottom wall or the top wall. The radiation or magnetic sensor(s) are electrically connected to a microprocessor unit capable of comparing the sensor signal with a given signal and to store sensor signal data over one or more cycles.

According to a particularly advantageous aspect of the invention the CPR apparatus comprises a valve means, in particular a solenoid valve means, controlled by means of compression depth and time data stored in the microprocessor memory related to the time at which the piston reached the Compression Depth during a reciprocating cycle, in particular an earlier reciprocating cycle.

The control of driving gas according to the method of the invention does not comprise the optional provision of driving gas to embodiments of the CPR apparatus of the invention at the end of the compression phase to push the piston back to its starting position.

SHORT DESCRIPTION OF THE DRAWINGS

The invention will now be explained by reference to preferred but not limiting embodiments thereof illustrated in a rough drawing, in which FIG. 1 is a sectional view of a first embodiment of the apparatus of the invention disposed on the chest of a patient shown in a transverse section at the level of the eight thoracic vertebra (T8) and viewed in a cranial direction;

FIGS. 6a-6c are graphs illustrating the effect of driving gas valve opening times on gas consumption in reaching and maintaining a desired compression depth against a given resilient force in CPR model experiments;

DESCRIPTION OF PREFERRED EMBODIMENTS

Example 1

Figure 1:
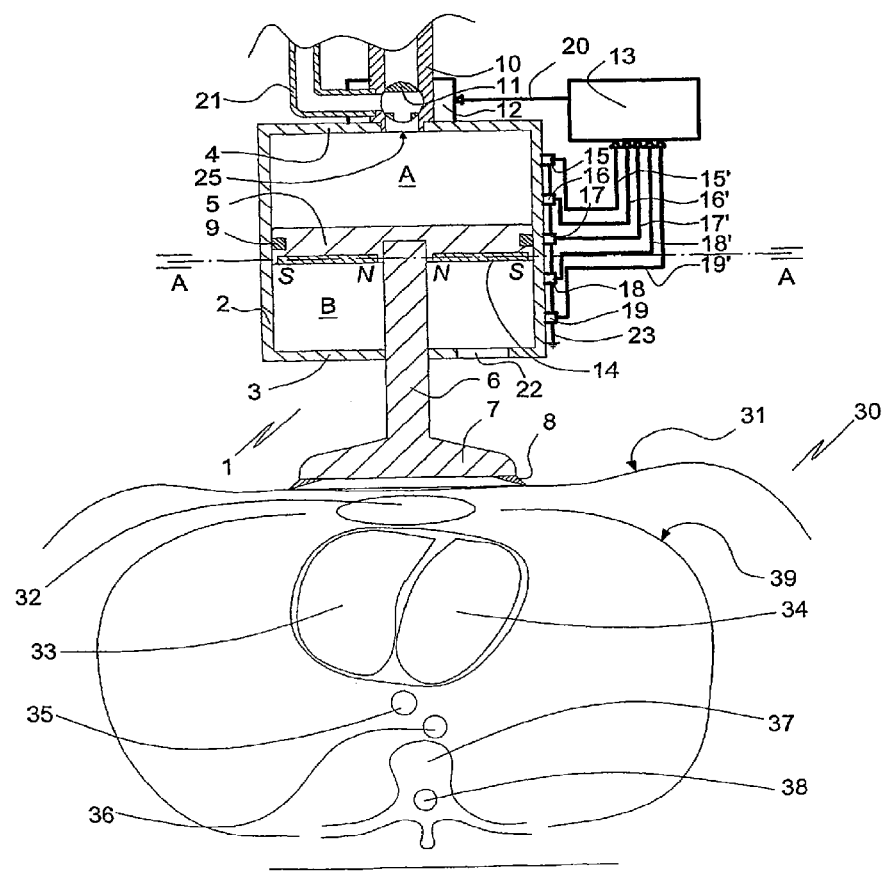
FIG. 1a is a detail view of the embodiment of FIG. 1, in the same view and enlarged.
FIG. 1b is a section A-A (FIG. 1) through a modification of the apparatus of FIG. 1.
FIG. 1c is a detail view of another modification of the apparatus of FIG. 1 showing solenoid valve control unit with a pair of solenoid valves.
Figure 1A:
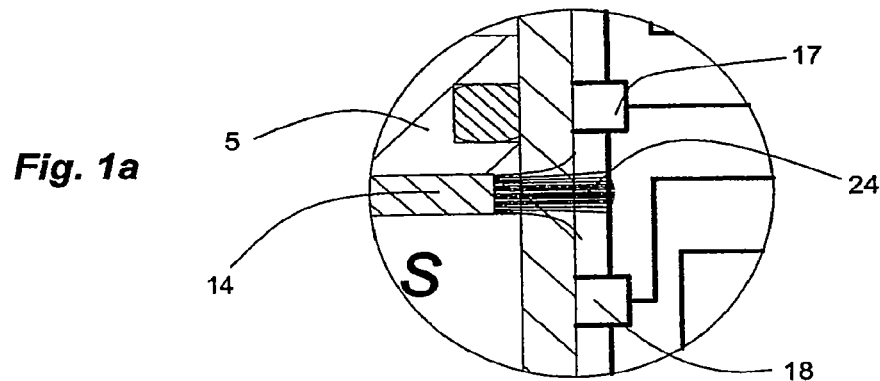
Figure 2A:
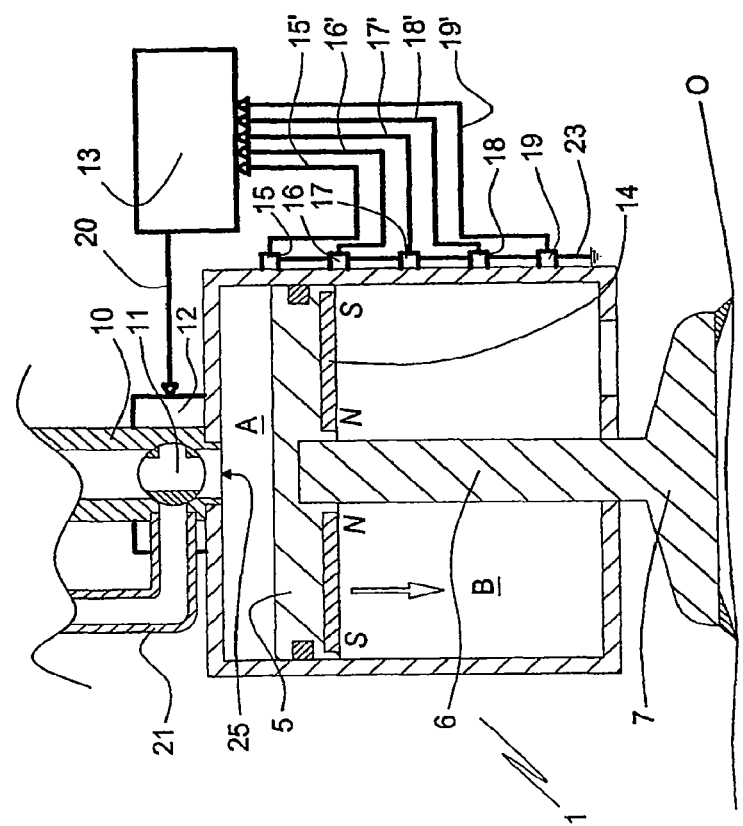
FIGS. 2a-2h show the embodiment of FIG. 1 and in the same view, in consecutive states of chest compression by reciprocating displacement of its piston and compressing pad.
Figure 2B:
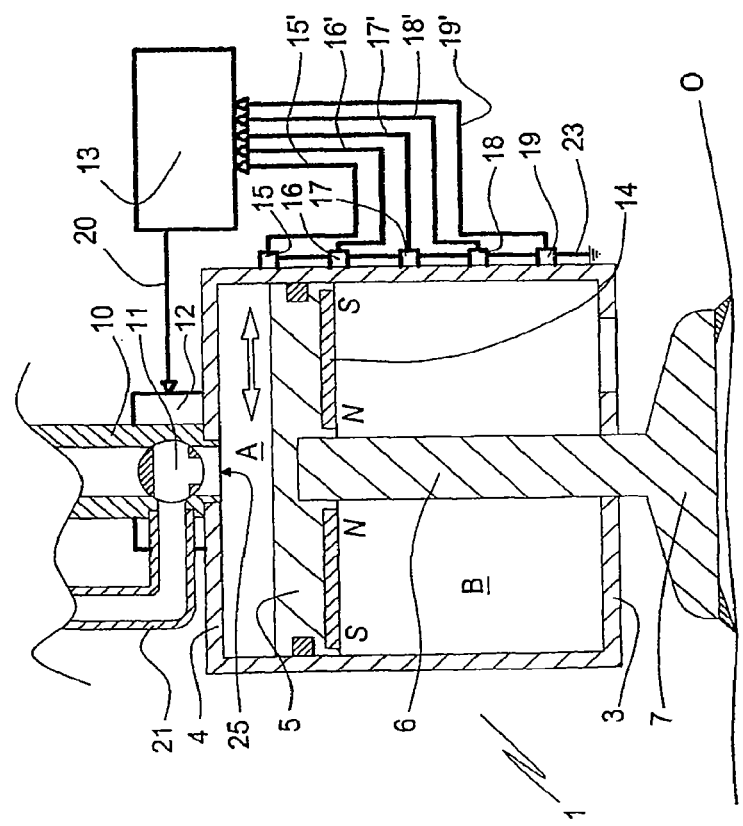
Figure 2C:
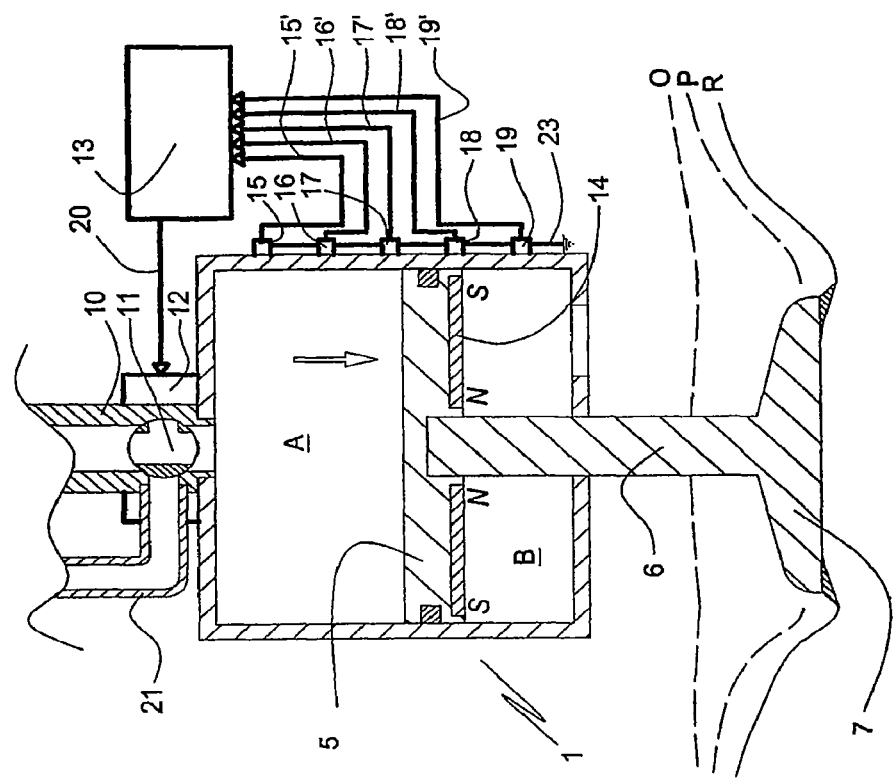
Figure 2D:
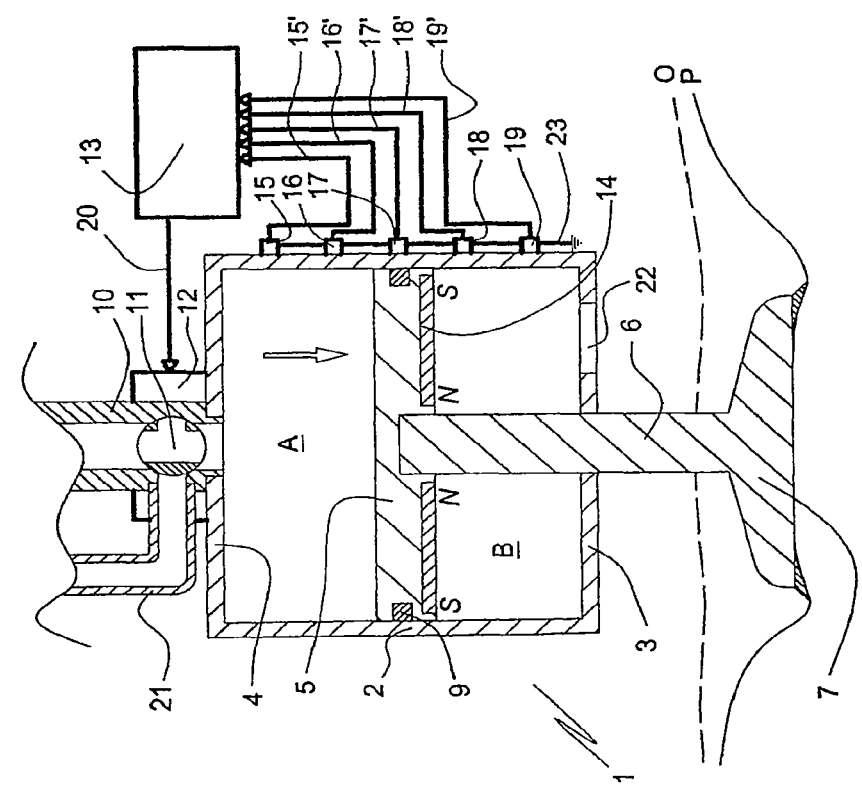
Figure 2E:
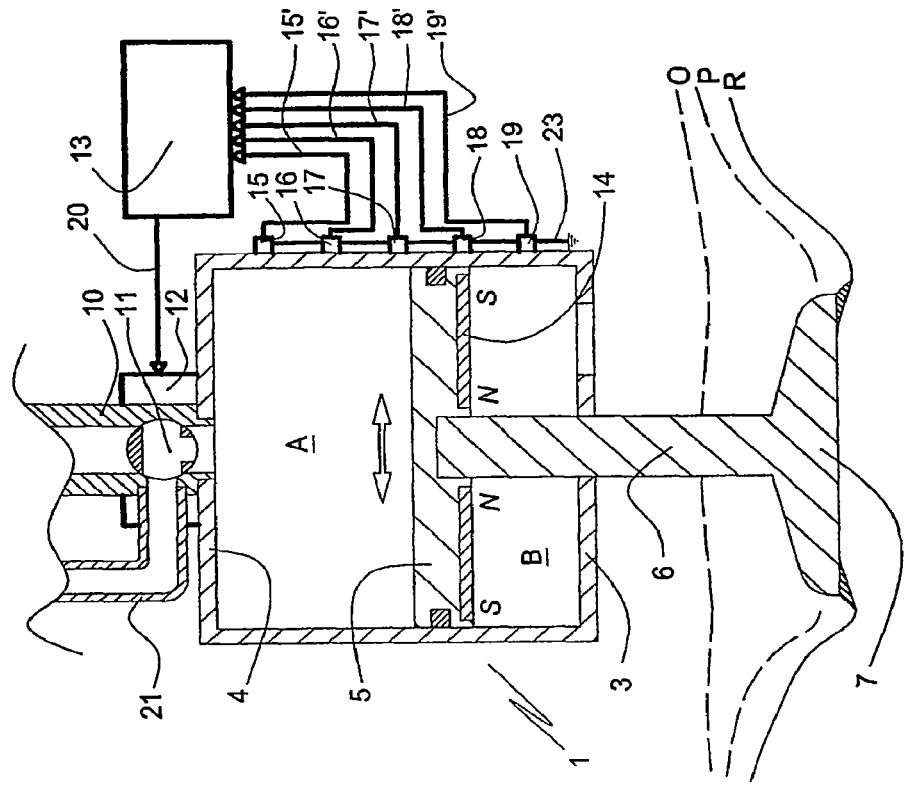
Figure 2F:
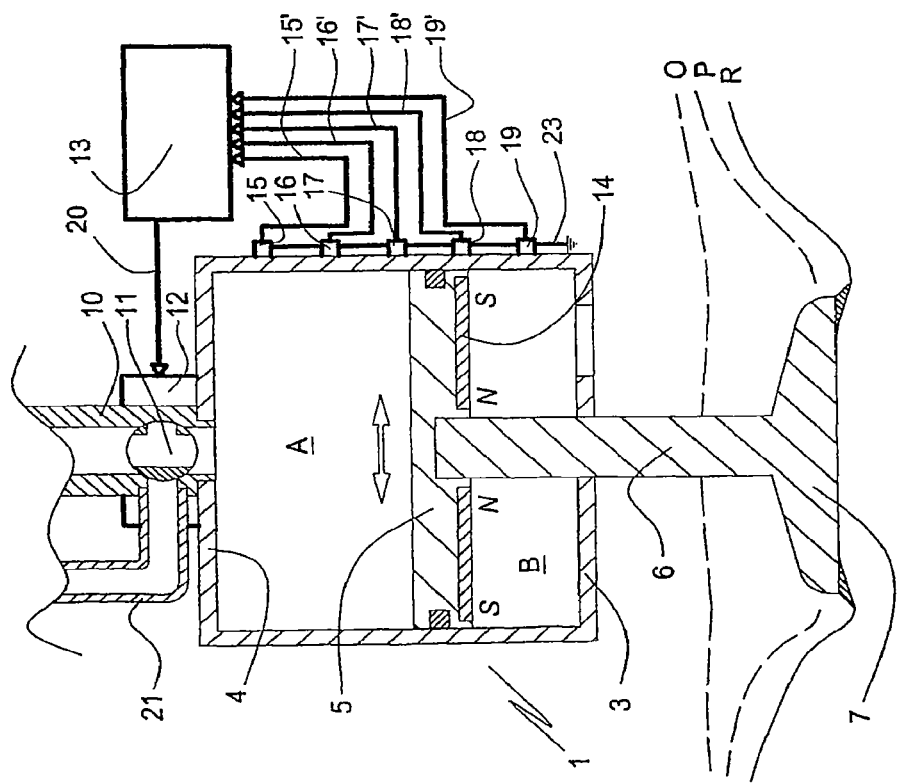
Figure 2H:
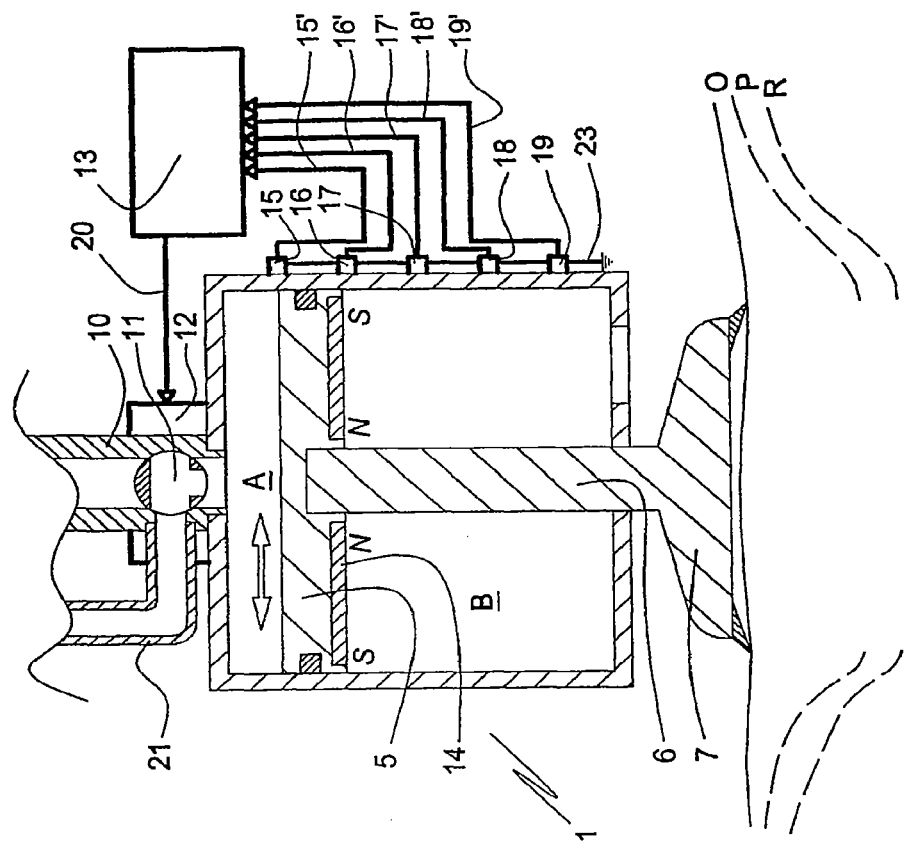
Figure 2G:
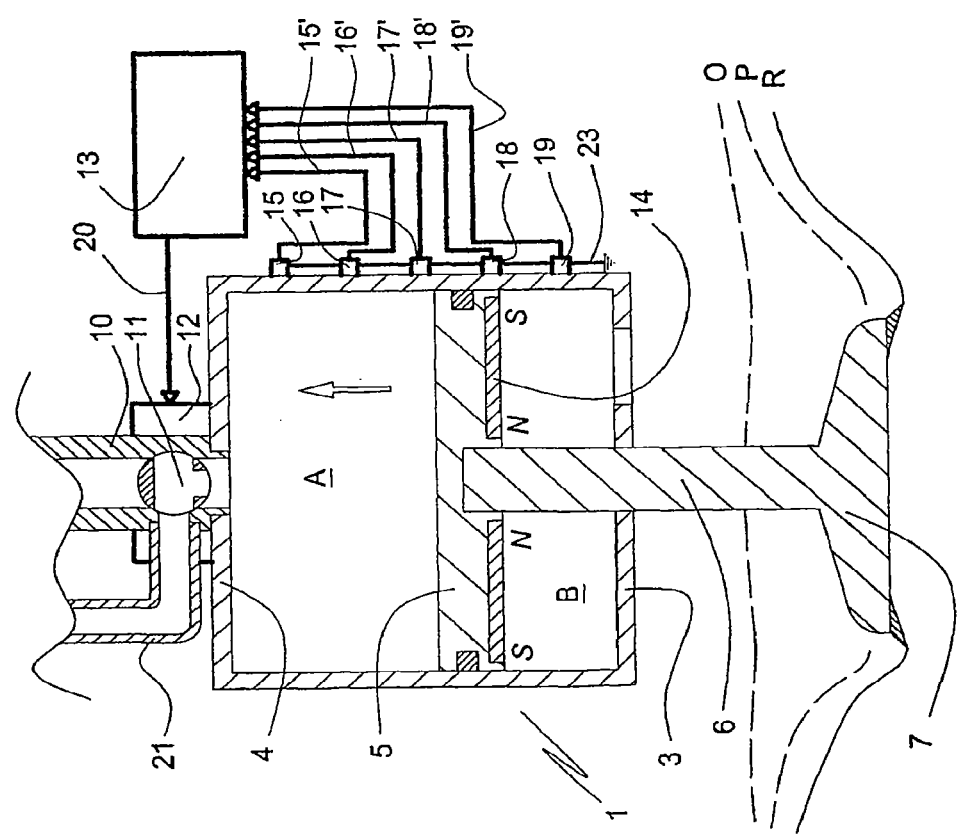
Figure 3:
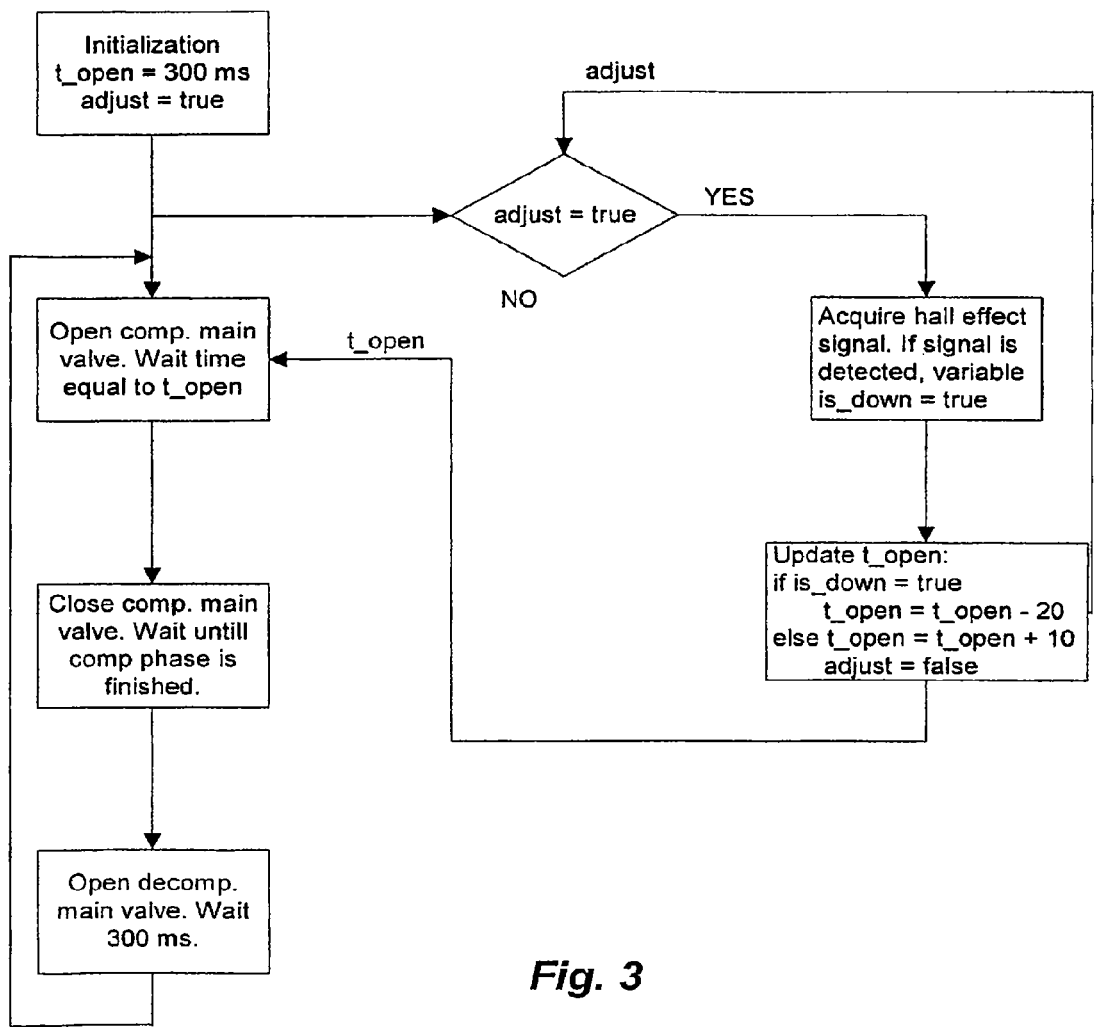
FIG. 3 is a block scheme of a solenoid valve control program.
Figure 4A:
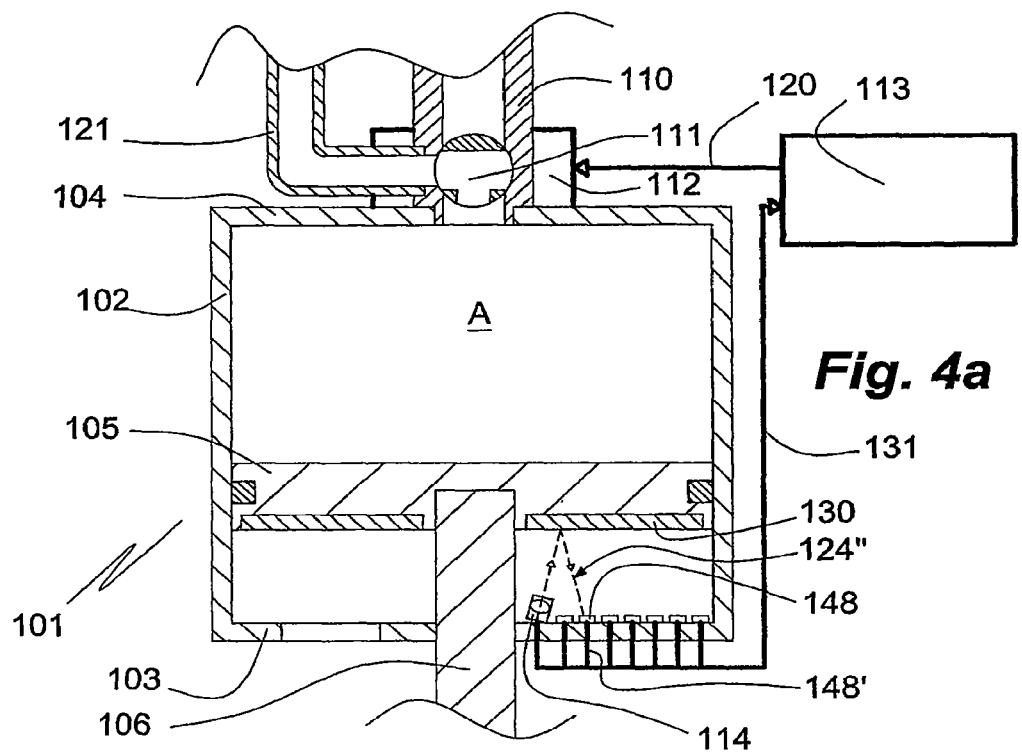
FIGS. 4a-4d show another embodiment of the apparatus of the invention, in the same view as in FIG. 1 and, in FIGS. 4c and 4d, partially enlarged.
Figure 4B:
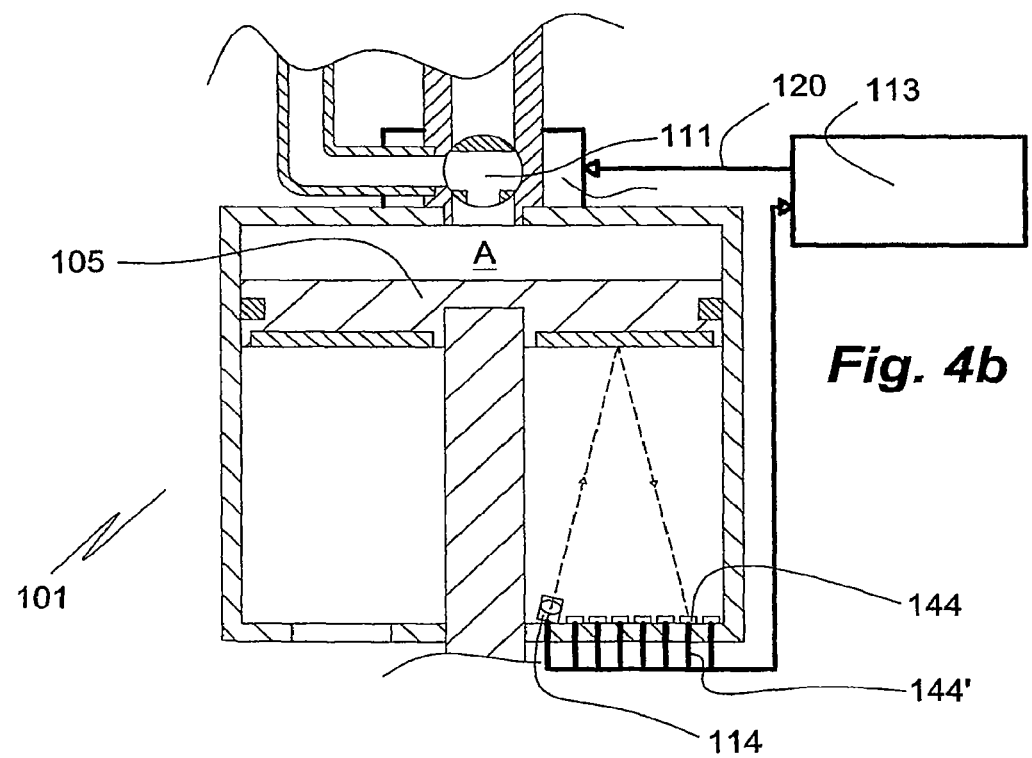
Figure 4C:
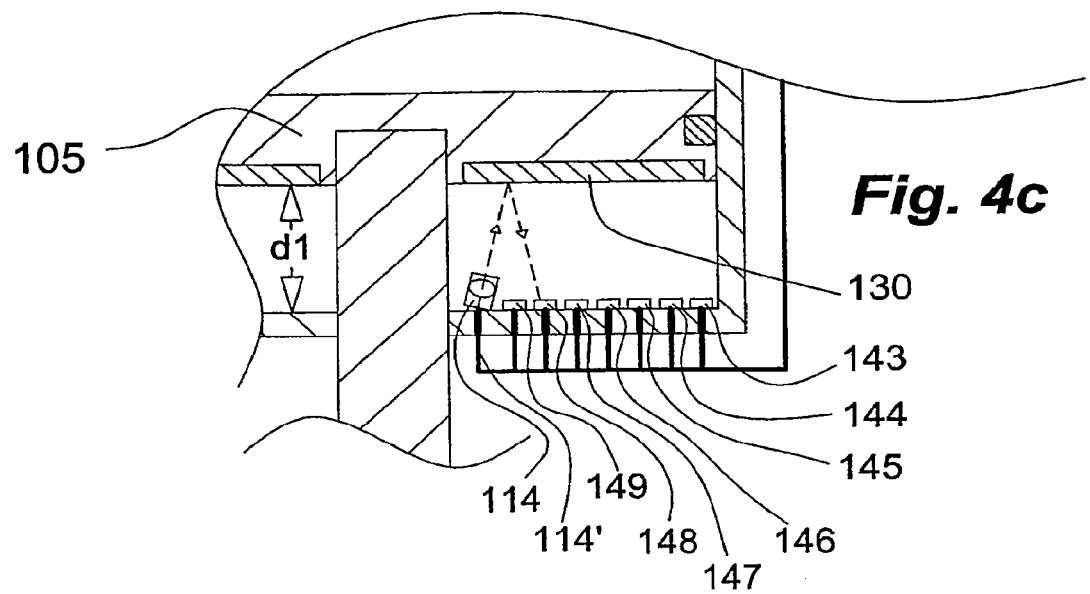
Figure 4D:
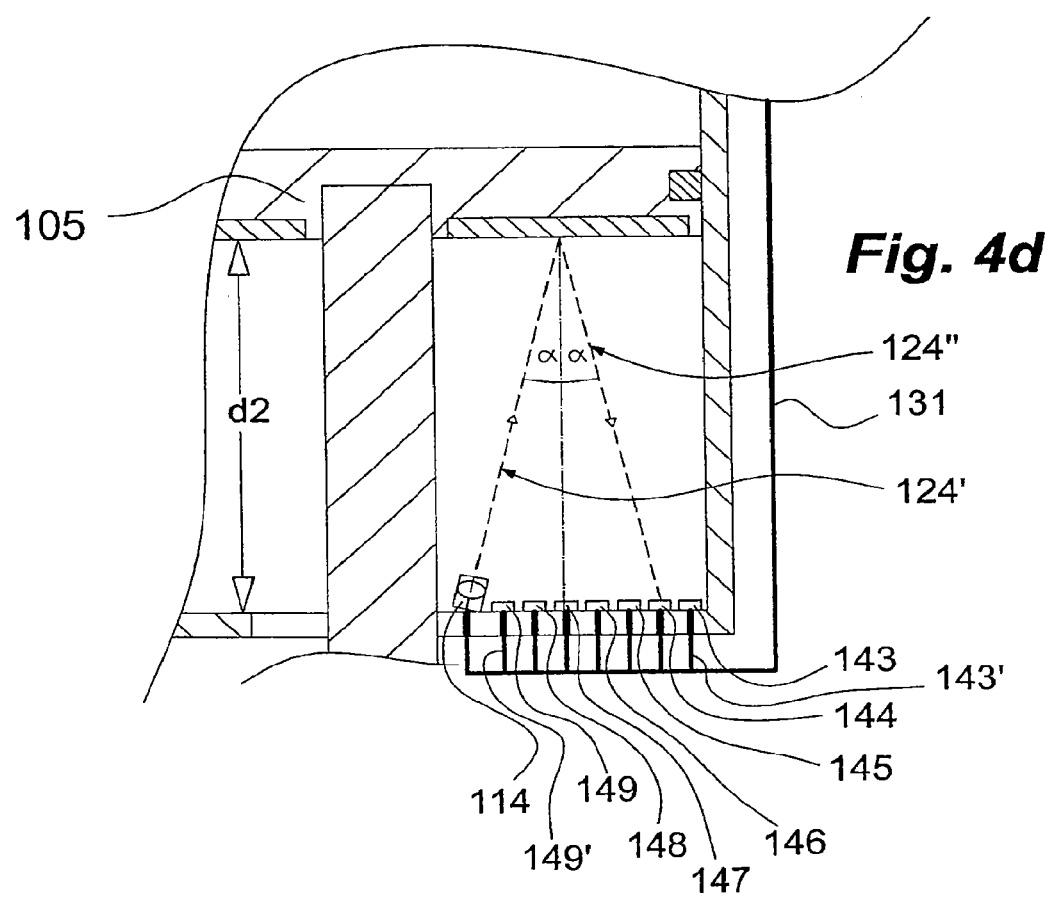

The embodiment of the apparatus 1 of the invention shown in FIGS. 1-2h comprises a cylinder housing of a diamagnetic material having a side wall 2, a bottom 3 and a top wall 4. A piston 5 with a circumferential sealing 9 is mounted in the housing and defines an upper compartment A and a lower compartment B. A plunger 6 extends downwards from the centre of the piston 5, passing through a central bore in the bottom 3 of the housing. At its free end the plunger 6 carries a chest compression pad 7 provided with a flexible circumferential lip 8. The piston 5/plunger 6/compression pad 7 is mounted displaceably in the cylinder housing. A neodymium magnet ring 14 is mounted at the lower face of the piston 5 with its south pole S facing the side wall 2. An array of unipolar Hall-Effect digital switches ("unipolar Hall switches") 15, 16, 17, 18, 19 is mounted at the outer wall of the cylinder 1 in an axial direction. The unipolar Hall switches 15, 16, 17, 18, 19 are characterized by their magnetic operating threshold. If the Hall cell of a switch 15, 16, 17, 18, 19 is exposed to the magnetic field of the south pole exceeding the operating threshold, the output transistor is switched on. If the field drops below the switching threshold, the transistor is switched off. One pole of each of the unipolar Hall switches 15, 16, 17, 18, 19 is grounded at 23 whereas the other is fed with 3 V DC by lines 15', 16', 17', 18', 19', respectively, connected to a microprocessor unit 13. In FIG. 1a the field lines 24 of the magnet's 14 south pole S are shown in respect of unipolar Hall switches 18, 19 to illustrate how the latter are influenced during a displacement of the plunger 6. The effect (Hall effect) by which the switches 15, 16, 17, 18, 19 are closed by the influence of the field of the magnet 14 allows to monitor the passage of the plunger by the microprocessor unit 13 (FIG. 3). During passage of the magnet 14 the circuit of the respective switch 15, 16, 17, 18 or 19 is closed, the current passing a closed switch being recorded by the microprocessor unit 13. After passage of the magnetic field the respective switch is again opened except for if the plunger stops in a position in which the magnetic field does cover it after stop. This allows the microprocessor unit 13 to keep track of the movement of the piston 5/plunger 6/pad 7 assembly and, in particular, its position at the end of its downward or, less important, upward movement, and to control the provision of compressed breathing gas to compartment A by the solenoid valve based on that position.

For reasons of simplicity number of unipolar Hall switches in the embodiment of FIGS. 1 to 2h is confined to five. An embodiment that allows to obtain fine tuning of positional control can comprise a higher number of unipolar Hall switches and/or have the switches disposed in the region of the compression depth level where the determination of position of piston 5/plunger 6/compression pad 7 is most important. Other Hall-effect switches like bipolar and omnipolar Hall-effect switches may be used for sending the field of magnet 14.

Figure 1B:
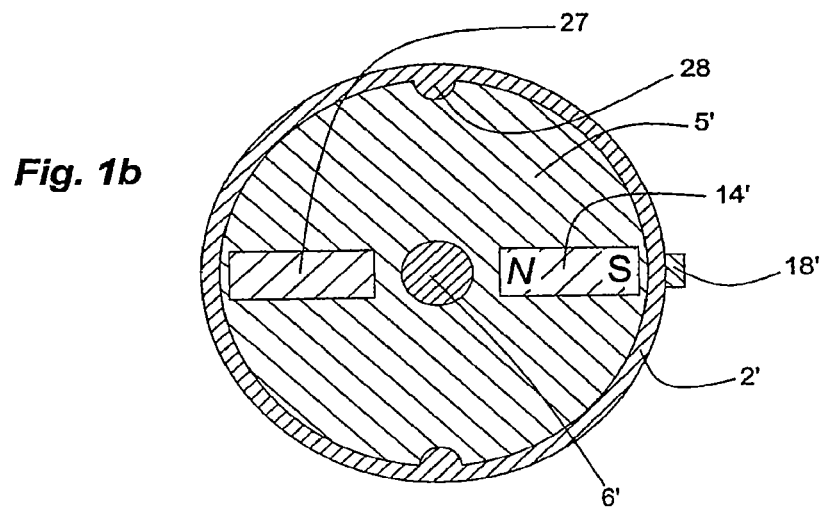

In a modification of the embodiment of FIG. 1 the ring magnet 14 is exchanged for a rod magnet 6' (FIG. 1b). For reasons of balance a counter weight 27 is mounted diametrically opposite to the magnet 6' at the lower face of the piston 5'. The use of a rod magnet 6' requires the arrangement of a means preventing rotation of the piston 5'. In FIG. 1b the rotation preventing means comprises two diametrically opposite axially extending flanges 28 protruding from inner face of the cylinder side wall 2' and co-operating with diametrically opposite axially extending slits in the side wall of piston 5'. Also shown is a Hall-effect switch 18' mounted at the outer face of the side wall 3' opposite to the south pole of magnet 14'.

Returning to the embodiment of FIGS. 1 and 2a-2h the upper compartment A of the housing is defined by the top face of the piston 5, a first portion of the side wall 2 of the housing, and the top wall 4 of the housing, whereas its lower compartment B is defined by the bottom face of the piston 5, the bottom face of the magnet 14, a second portion of the side wall 2 and the bottom wall 3. An opening 22 in the bottom wall 3 allows air to enter into compartment B or to be expelled from it depending on the direction of displacement of the piston 5.

Figure 1C:
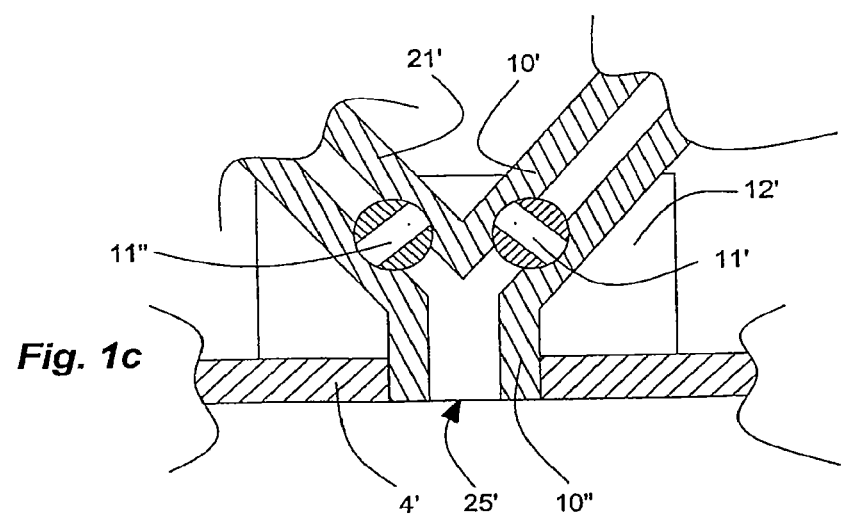

A tube 10 for providing compressed breathing gas from a gas supply such as a gas cylinder or other container of compressed breathing gas (not shown) is mounted at and communicates with an opening 25 in the top wall 4. Near the opening 25 a venting tube 21 branches off from tube 10. Tube 21 can be put in communication with a breathing mask (not shown) borne by the patient under cardiopulmonary resuscitation. A three-way solenoid valve 11 controlled by a solenoid control unit 12 is mounted in the lumen of tube 10 at the branching of the venting tube 21. In a first position P1 the solenoid valve 11 allows compressed breathing gas to enter compartment A through opening 25. In a second position P2 the solenoid valve 11 allows to vent compressed air in compartment A through venting tube 22. The solenoid valve 11 is only shown schematically in the Figures; its design allows switching between positions P1 and P2 without passing an intermediate position in which the lumina of tubes 10 and 21 and the compartment A are in simultaneous communication. The solenoid valve is actuated by a solenoid valve control unit 12 receiving actuation signals from the microprocessor unit 13 via line 20. The microprocessor unit 13 and the solenoid valve control unit 12 are energized by a dry battery (not shown). The three-way solenoid valve 11 of the embodiment of FIGS. 1 and 2a to 2h can be exchanged for a pair of solenoid valves 11', 11" actuated by a solenoid valve control unit 12' (FIG. 1c). Reference numbers 4', 10', 21' and 25' identify elements corresponding to elements 4, 10, 21 and 25, respectively, of the embodiment of FIGS. 1 to 2h.

After leaving the gas cylinder the compressed breathing gas is decompressed in controlled manner (not shown) to a working pressure, which is kept about constant during CPR. The gas of working pressure is suitable held in a reservoir from which the gas of working pressure is adduced to the compartment A via tube 10 so as to provide it at an about constant gas pressure over time. This allows the provision of a controlled compression force via the piston 5, the plunger 6, and the pad 7 to the chest of a patient. Since the adduction of compressed gas through tube 10 and the build-up of gas pressure in compartment A is a dynamic process governed by the pressure of the gas in the gas reservoir, the gas pressure in the compartment 10 (the pressure of the "provided" driving gas) is not in equilibrium with the pressure of the driving gas at the source over an initial portion of the compression phase.

The compression pad 7 is loosely placed on the chest 30 of a person to be provided chest compressions (FIG. 1). The person is in a recumbent position with the pad 7 placed on the skin 31 above the sternum 32. Reference numbers denote: 33, right ventricle; 34, left ventricle; 35, esophagus; 36, descending aorta; 37, body of the eight thoracic vertebra (T8); 38, spinal cord; 39 left arc of ribs.

The function of the apparatus of the invention will now be explained with reference to FIGS. 2a through 2h.

The position at the start of dispensation of chest compression is shown in FIG. 2a, which corresponds to FIG. 1 except for that only the skin 31 of the patient's chest in the sternal region is shown. In the Figures the uncompressed level of the skin 31 at the application site of the pad 7 is designated O. The solenoid valve 11 is in the venting position P1 and the plunger is in an unloaded state. By opening of the venting valve 11 (valve position P2) compressed air is made to flow from the gas cylinder to tube 10 and to enter compartment A through opening 25. The increasing air pressure in compartment A starts to force the piston 5 downwards in the direction of bottom wall 3 (FIG. 2b; start of downward movement of piston 5 indicated by an arrow). At start the south pole S of the magnet 14 is disposed between Hall switches 15 and 16. During its downward movement (FIG. 2c; valve 11 in position P2; skin level at intermediate position P during downward movement) the south pole S of the magnet 14 passes Hall switches 16, 17 and stops at the level of switch 18 (skin level R at initial full compression=Compression Depth in an initial cycle of CPR). It stops at because, at this level, the compression force of the compressed gas acting on the piston 5 transferred by the pad 7 to the patient is balanced by the resilient counterforce of the compressed chest tissues. As explained above, the microprocessor unit 13 keeps track of the position of the piston 5 during its downward (and upward, if desired) movement, and recognizes the exact moment at which the piston 5/plunger 6/rod 7 assembly has reached its extreme position during its downward movement (FIG. 2d, indicating the infinitesimal last downward movement of piston 5/plunger 6/rod 7 assembly prior to stop with the valve 11 in position P1; FIG. 2e, the moment of stop with the valve 11 in position P1; and, at the same moment, FIG. 2f, an immediate switch of the valve 13 from position P1 to P2. As explained above and if desired, the switch of the solenoid valve 11 from P1 to P2 can be made to occur slightly earlier, that is, prior to the piston 5/plunger 6/rod 7 assembly reaching its downward stop position by programming of the microprocessor 13 correspondingly. The recognition of the time when the piston 5/plunger 6/rod 7 assembly reaches its lower end or bottom position moment thus is used for control of the solenoid valve so as to switch it from position P2 to P1. The flow of compressed gas into compartment A is stopped at the moment where the piston 5/plunger 6/rod 7 assembly reaches the desired extreme position (Compression Depth) or slightly before that moment. Thereby the provision of driving gas is optimized and thus economized. This is of particular importance for a CPR apparatus to be used outside facilities like a hospital where practically unlimited resources of compressed gas of various kind are available. In the state of the apparatus shown in FIG. 2f compartment A is vented via tube 21. If the driving gas is a breathing gas the vented gas or a portion thereof, which is still of a slightly higher pressure than ambient air, can be adduced to the patient's lungs via a breathing mask or by intubation (not shown). The venting of compartment A stops the load on the piston 5/plunger 6/rod 7 assembly (FIG. 2g) and thus the compression of the patient's chest. The resilient nature of the chest makes it expand and push the piston 5/plunger 6/rod 7 assembly back to its start position (FIG. 2h).

The microprocessor unit 13 of the apparatus of the invention is programmed in a manner so as to sample and store positional data over one or several cycles, and to use such data for control of a later cycle.

For reasons of simplicity and to better illustrate the principles of the invention the apparatus the invention shown in FIGS. 1 to 2h has been simplified in respect to commercially available apparatus of this kind in regard of ancillary features. Thus, the upward movement of the piston 5/plunger 6/rod 7 assembly of this embodiment of the apparatus of the invention is passive, that is, driven by the resilient force of the patient's chest, whereas it can be advantageously be driven by means of the compressed breathing gas used in the apparatus. In such case a substantially more complex arrangement of valves and gas lines for adducing compressed gas to compartment B and venting it from there is required. The provision of and additional pressure means for actively, that is, substantially independent of the resilient forces of a compressed chest, returning the piston to its start position does however not change the principles of the present invention, which even might be used to optimize the use of compressed gas in the displacement of the piston 5/plunger 6/rod 7 assembly in such upward (decompressing) direction.

In a second embodiment of the CPR apparatus of the invention 101 shown in FIGS. 4a to 4d the position of the piston 105 and thus the compression depth is determined by means of a source of visible light 114 and a number of photo detectors 143, 144, 145, 146, 147, 148, 149, all disposed in a radial direction, with the light source 114 innermost, on the inner face of bottom wall 103. The light source 114 is a red light photodiode whereas the photo detectors 113-119 are silicon based photodiodes operated in photoconductive mode.

The narrow and substantially parallel beam of light 124' of the photodiode 114 is directed at the lower face of the piston 114, which is provided with a ring mirror 130, at an angle .alpha. and in the same a radial direction in respect of the piston 105 axis as that of the disposition of photo detectors 113-119. The incident beam 124' is reflected at the same angle .alpha. in the direction of photo detectors 113-119 disposed on the bottom 103. The distance between the inner face of the bottom 103 and the lower face of the piston 105 provided with the mirror element 130 determines which of the photo detectors 143-149 is hit by the reflected beam 124''. In a position of the piston 105 near the bottom wall 103 (distance d1, FIG. 4c) the reflected beam 124'' hits the next but innermost photo detector 148, whereas in a position of the piston near the top wall 104 (distance d2, FIG. 4d) the next but outermost photo detector 144 is hit. During a downward movement of the piston 105 the reflected beam 124'' thus will sweep, depending on its start position and its end position (Compression Depth position) over all or only some of the photo detectors in a radially inward direction. The photo diode 114 and the photo detectors 143, 144, 145, 146, 147, 148, 149 are connected to a microprocessor unit 113 via separate conductors 114', 143', 144', 145', 146', 147', 148', 149', respectively, which are bundled in a cable 131. The microprocessor 113 uses the signals from the photo detectors 143-149 in a time frame to control gas flow in the apparatus 100 by a solenoid valve 111 operated by a solenoid control unit 112 in a manner corresponding to that described in Example 1 for the electric signals generated by the Hall-effect switches 15, 16, 17, 18, 19. In FIGS. 4a-4d reference numbers 106, 110, 120, 121 refer to a plunger 106 carrying a chest compression pad (not shown), a tube 110 for adducing compressed breathing gas, to a electrical connection 120 between the microprocessor unit 112 and the solenoid control unit 112, and to a tube 121 for venting compressed breathing gas used for displacement of the piston 105, respectively.

Figure 5:
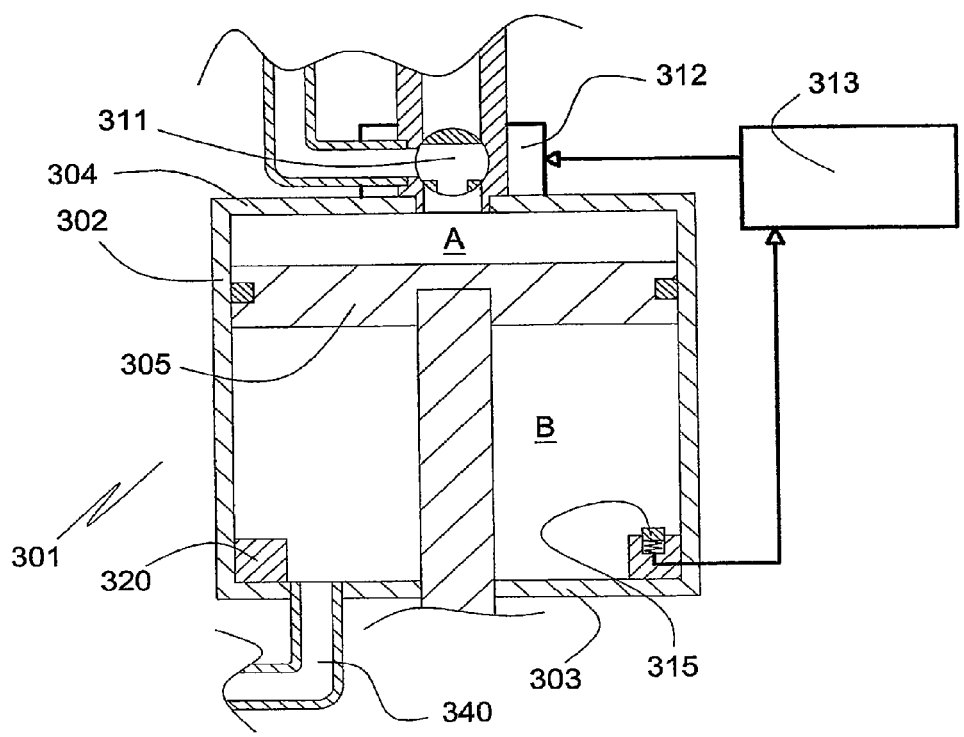
FIG. 5 shows a further embodiment of the apparatus of the invention, in the same view as in FIG. 1.

In a third embodiment of the invention shown in FIG. 5 the stroke of the piston 305 is limited by an annular stop 320. At its lower extreme position the piston 305 hits and thereby closes a contact switch 315 of an electrical circuit comprised by a microprocessor unit 313. The microprocessor unit 313 thereby receives information about the moment at which the Compression Depth is reached. Based on this information the microprocessor's 313 issues a closing command to the control unit 312 of solenoid valve 311, in particular in a following cycle prior to the expected time of contact. In this embodiment the provision of a gas inlet tube 340 to provide driving gas to the closed lower chamber B of the cylinder housing 302, 303, 304 illustrates the principle of assisted piston 305 return that can be applied to all embodiments of the invention, if desired.

Example 2

Solenoid Valve Control Program

In the following an example of a simple main valve control program is provided (Table 1). In the example consideration is given to one Hall effect element (Hall switch), which is placed at about a desired level of piston 5/plunger 6/rod 7 assembly stop (bottom level). Time open for the decompression main valve is set to 300 ms; while this parameter is fixed in the Example, it could be controlled in precisely the same way as time open for the compression main valve.

TABLE 1

```
Initialize:
set     t_open = 300                        [ms]
set     adjust = true
(Parallel process #1, controls main valves)
While true do
        is_down = false
        main_valve_comp = true              /opens compression main valve
        wait       t_open                   /holds main valve open for t_open ms
        main_valve_comp = false             /closes compression main valve
        wait    300 − t_open                /wait the rest of the compression
phase
        main_valve_decomp = true            /opens decompression main valve
        wait       300                      /waits until whole cycle is complete
        main_valve_decomp = false           /closes decompression main valve
        if adjust = true
                if is_down = true
                        t_open = t_open − 20            /decreases t_open
```

TABLE 1-continued

```
            else
                    t_open = t_open + 10              /increases t_open
                    adjust = false                    /adjustment is now
            complete
            end if
        end if
end while
(Parallel process #2, samples hall_element_signal input and updates variable "is_down")
while adjust = true do
            hall_effect_sample = read_digital_input_signal_of_hall_effect_element
            is_down = is_down or hall_effect_sample   /true if piston has
reached
end while                                             /hall element during
                                                      cycle
```

When the program starts the program variable (t_open), which controls the time the air supply port for the compression phase is open, is set to 300 ms, which is the maximum possible value. The apparatus then performs one cycle (compression and decompression) with this setting. During the cycle the signal from the Hall effect element is sampled. If the piston reaches the bottom of the cylinder it will be registered by the Hall effect sensor signal as a high voltage, sampled by the function "read digital input signal_of_hall_effect_element" and then written to the variable is_down. is_down is the variable that indicates whether the piston has reached its bottom position during the cycle, and then determines which adjustment of t_open shall be performed. If a trigger was detected (and is_down set to true), than the variable t_open is lowered by 20 ms. This is repeated for every cycle until there is no trigger detected. During this last cycle the piston is likely to have stopped just before it reached the Hall effect element, such as a few millimeters from demand position. As is_down now is false the variable t_open is increased by 10 ms, which makes the piston move a little bit further down next cycle; this is then considered to be the final position at which the update procedure stops (since the variable adjust is set to false it cannot become true again). This setting will be used for the rest of the treatment or may be changed after some time such as, for instance, 10 minutes from start, to adapt the compression to the aforementioned change in physical properties of the chest. A block diagram of the program is shown in FIG. 3.

Example 3

The effect of the method of the invention in the control of compressed driving gas is demonstrated by three experiments illustrated in FIGS. 5a-5c. The experiments were carried out with an air-driven reciprocating CPR device mounted on a test bench. The CPR apparatus comprises a compression cylinder 208 comprising an upper compartment 219 and a lower compartment 220 delimited in respect of each other by a piston 216 arranged displaceably in the cylinder 208. The apparatus further comprises a breast compression pad 210 attached to the piston 216 via a shaft 211, a valve control unit 212 with a valve manifold, and a gas line 213 supplying driving gas from source of compressed gas (not shown) to the compression cylinder via the valve control unit 212. The stroke (str) of the piston 216 is limited to 55 mm by means of upper 217 and lower 218 stroke limiters disposed in the upper and lower compartments, 219, 220, respectively. The gas pressure in the upper compartment 219 is measured by a manometer 214. The test bench comprises a flat base 201 on which the CPR apparatus is mounted via a pair of legs 209. The compression pad 210 abuts a top face of a sternal plate 204 resting on a support 202 via an interposed force sensor 203. The support 202 rests displaceable in a vertical direction on the base 201 via compression coil means 205, which mimic a resilient chest. A linear sliding rail 206 fixed at the base 201 allows to read the position of the sternal plate 204 and the compression pad 210 by means of a linear slide guide 207 running on the rail 206. The slide guide 207 comprises a position sensor. As indicated by reference numbers 203', 207', 212' and 214' signals from the force sensor 203, the position sensor 207, the valve control unit 212 and the manometer 214 are electrically transferred to a control unit 215 in which they are stored and from which the can be recalled and displayed. The resisting force of the compression coil means 205 against further compression at a Compression Depth of about 50 mm was set to about 500 N (FIG. 5a, 477 N) or half of that value, about 250 N (FIG. 5b, 239 N; FIG. 5c, 230 N). These and other parameter values are listed in Table 2. In all experiments the pressure of the driving gas fed to the compression cylinder was 2.91 bar.

TABLE 2

| Exp. # | Reciprocating frequ., 1/min | Max. cylinder pressure, bar | Force (N) | Compr. phase, sec | Decompr. phase, sec | Inlet valve open, sec | Compr. depth, mm |
|---|---|---|---|---|---|---|---|
| a | 98 | 2.91 | 477 | 0.31 | 0.30 | 0.31 | 52.1 |
| b | 99 | 2.88 | 239 | 0.31 | 0.30 | 0.31 | 56.0 |
| c | 99 | 1.36 | 230 | 0.30 | 0.31 | 0.09 | 55.5 |

Experiment (a), FIG. 5a, reflects the situation at the start of CPR, that is, during the first compressions administered to a patient. To provide optimal treatment it is necessary to obtain full compression, that is, a Compression Depth of about 50 mm for the average adult person, right from start and at an adequate rate of about 100 compressions per minute and even more. For this reason the minimum pressure of the driving gas is set to about 3 bar or more. This suffices to develop a compression force of about 500 (477 N in the experiment), by which the compression coil means 205 are compressed to a full stroke (str, FIG. 6), the lower stroke limiter 218 being reached at point L in FIG. 5a.

Figure 6B:
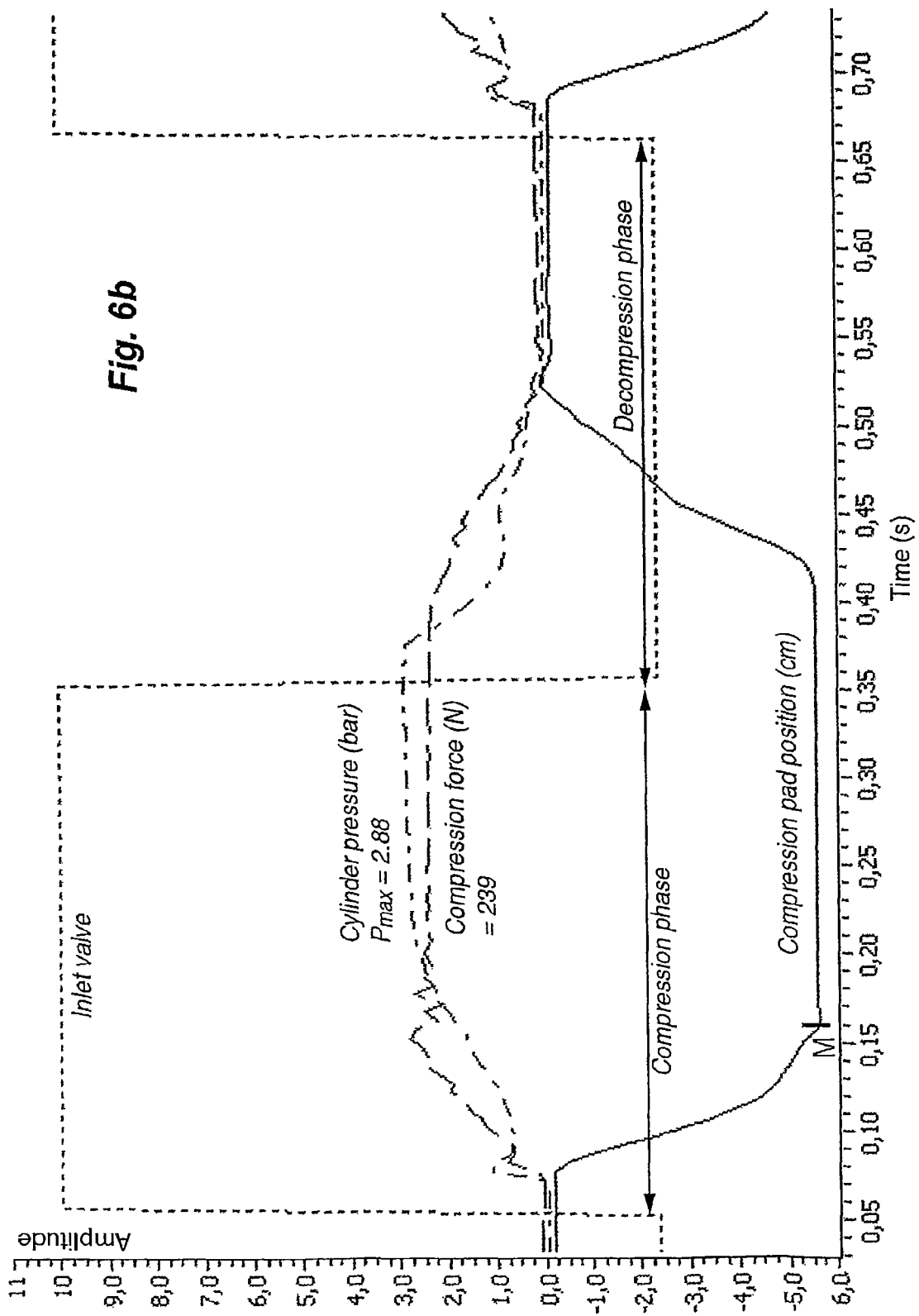
Figure 6C:
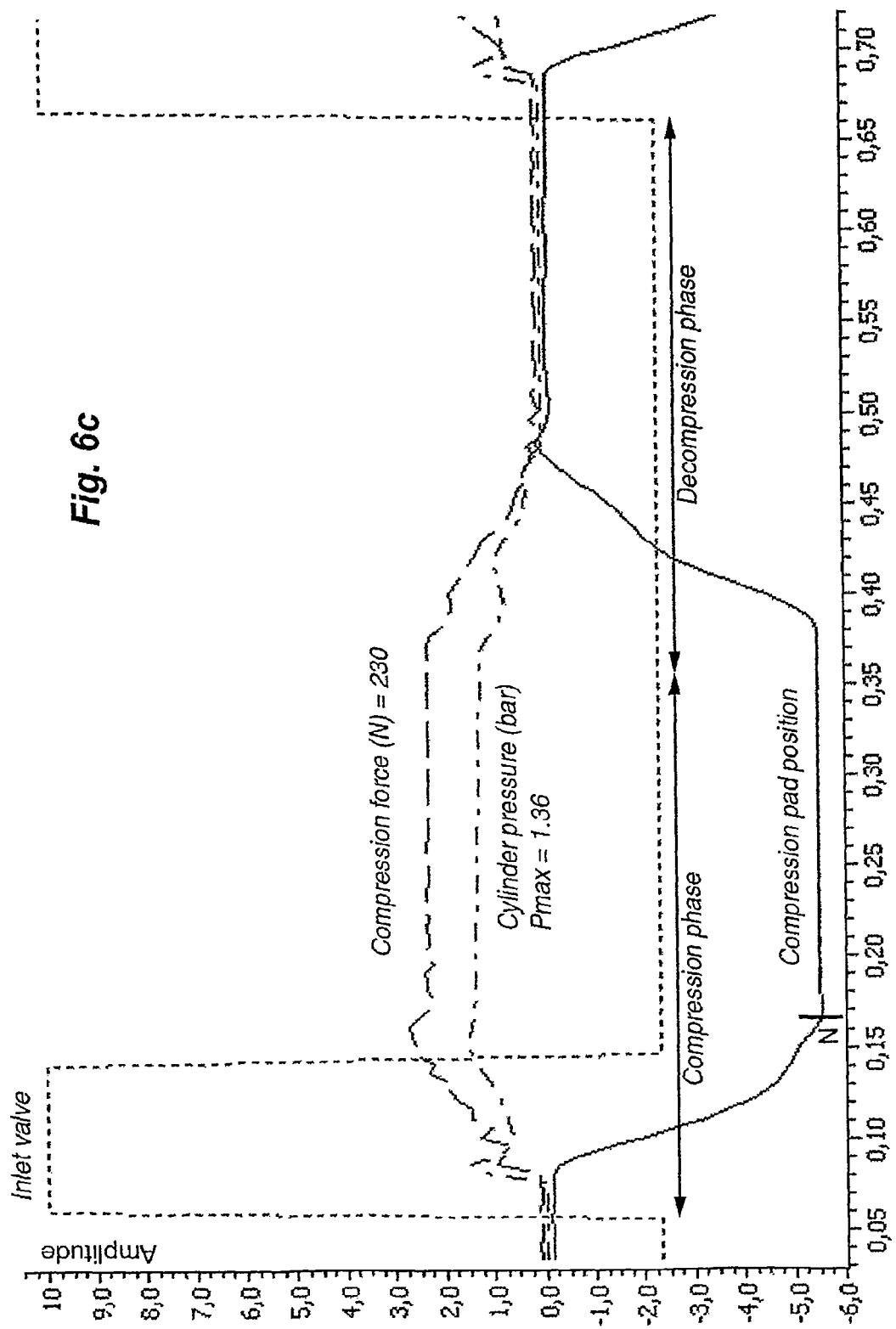
Figure 7:
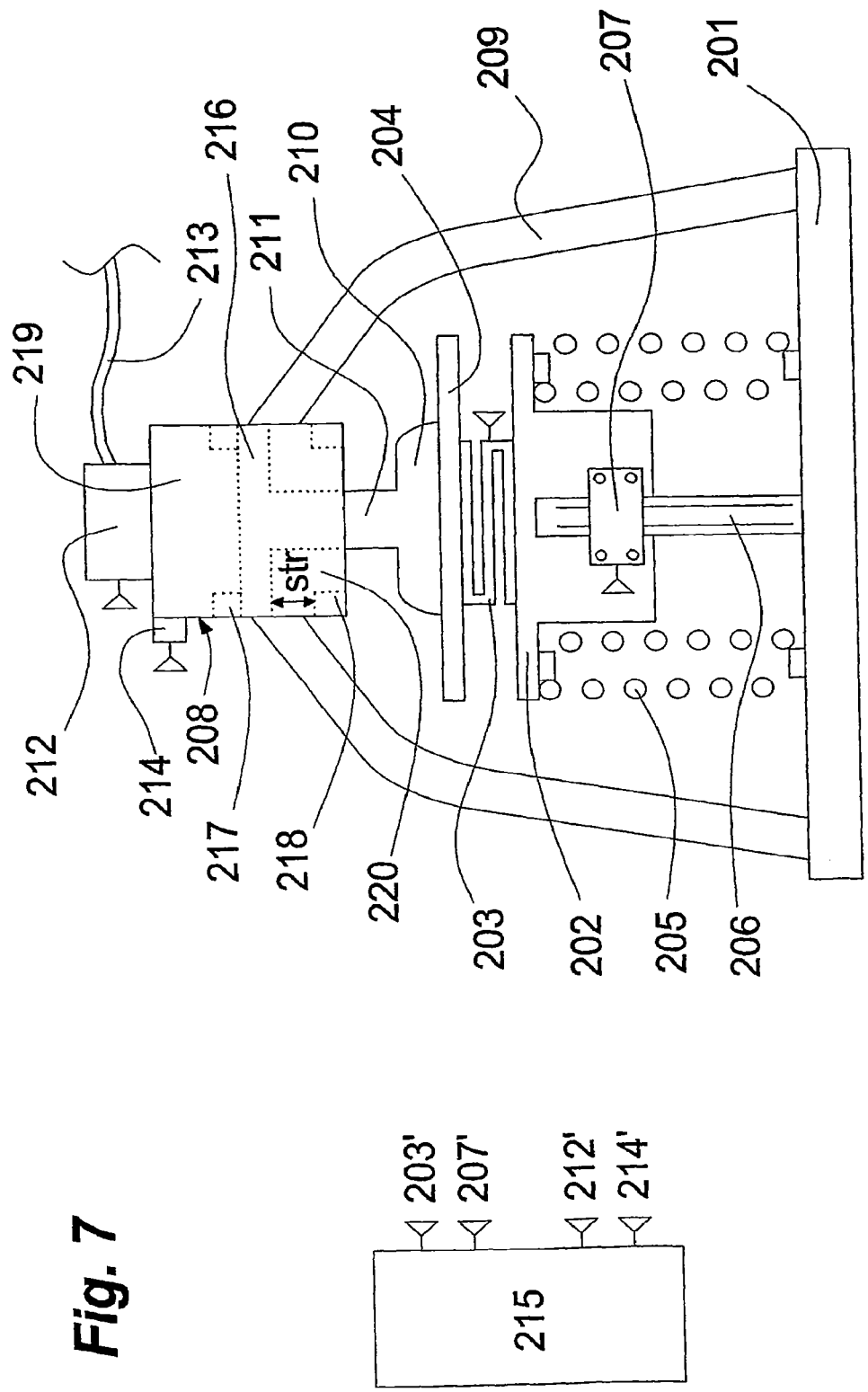
FIG. 7 is a rough sketch of the compression testing apparatus used in the experiments illustrated in FIGS. 6a-6c.

Experiment (b), FIG. 5b, reflects the situation after provision of compressions to a patient for a few minutes. During this time period the resistance of the chest diminishes by about 50%. The force of compression necessary to obtain a desired Compression Depth of about 50 mm thus is substantially reduced. In this experiment the resistance of the compression coil means 205 is set to about half (239 N) of the resistance in experiment (a). A compression profile similar to that of experiment (a) is obtained, except for the downward stroke occurring considerably faster, the lower stroke limiter 218 being reached at M. In both experiments (a) and (b) the driving gas inlet valve is open during the entire compression phase. It is closed simultaneously with the opening of the venting valve, by which the pressure in the compression chamber is released to allow the piston 216 and the compression pad 204 return to their starting position defined by upper stroke limiter 217. This return movement is supported by means of driving gas being fed to a lower chamber 219 in the housing (FIG. 6).

In experiment (c), FIG. 5*c*, substantially the same time v, compression pad displacement curve is obtained as in experiment (b). Experiment (c) differs from experiment (b) only in that the valve by which driving gas is adduced to the upper chamber 219 is kept open for a comparatively short time only. It is made to close at N (FIG. 6) even before the Compression Depth is reached. The final or maximum gas pressure in the compression compartment is thereby limited to about half of the pressure in experiment (b), and a corresponding saving of driving gas is obtained.

Experiments (a) to (c) demonstrate that up to 60 percent and even up to about 70 percent of driving gas can be saved by the method and the apparatus of the invention. This has been confirmed in in-vivo experiments in a pig model.

What is claimed is:

1. A method of sensing a compression depth in a reciprocating apparatus for cardio-pulmonary resuscitation (CPR) having a reciprocating plunger assembly within a non-reciprocating housing, the method comprising:
    sensing, with an array of magnetic sensors on the housing and for different positions of the plunger assembly, a magnetic field emanating from a permanent rod magnet reciprocating with the plunger assembly, the permanent rod magnet having a pole facing the housing, the array of magnetic sensors including more than two magnetic sensors positioned between an upper extent of a stroke of the plunger assembly and a lower extent of the stroke, and the plunger assembly including a counterweight diametrically opposite to the rod magnet;
    creating an electrical signal in at least one of the magnetic sensors by sweeping the at least one of the magnetic sensors with the magnetic field; and
    transmitting the signal to a microprocessor unit that records an arrival time of the signal.

2. The method of claim 1, further comprising driving the plunger assembly by a compressed gas.

3. The method of claim 2, further comprising utilizing the signal, by the microprocessor unit, to control the compressed gas driving the plunger assembly.

4. The method of claim 1, further comprising utilizing the signal, by the microprocessor unit, to control reciprocation of the plunger assembly.

5. An apparatus for cardio-pulmonary resuscitation (CPR) comprising:
    a cylinder housing having a diamagnetic wall;
    a diamagnetic plunger assembly configured to reciprocate within the housing;
    a rod magnet configured to emit a magnetic field and configured to reciprocate with the plunger assembly, the rod magnet having a pole facing the housing, and the plunger assembly including a counterweight diametrically opposite to the rod magnet; and
    an array of magnetic sensors on a surface of the housing, the array of magnetic sensors including more than two magnetic sensors positioned between an upper limit of a stroke of the plunger assembly and a lower limit of the stroke, each of the sensors in the array of magnetic sensors being configured to detect when the magnetic field exceeds a threshold during each of a plurality of reciprocation cycles and, when the magnetic field exceeds the threshold, to transmit a signal.

6. The apparatus of claim 5, further comprising a microprocessor connected to the array of magnetic sensors and having a memory, the microprocessor being configured to receive the signals and to store the received signals in the memory.

7. The apparatus of claim 6, in which the array of magnetic sensors is further configured to sense a current position of the plunger assembly.

8. The apparatus of claim 7, further comprising a valve configured to control a volume of pressurized gas entering the housing, the valve further being configured to be controlled by the microprocessor based on the stored signals and the current position of the plunger assembly.

9. The apparatus of claim 8, in which the housing comprises a first chamber at a first side of the housing and a second chamber at a second side of the housing that is opposite the first side.

10. The apparatus of claim 9, further comprising a second valve configured to control a second volume of pressurized gas leaving the second chamber of the housing, the second valve further being configured to be controlled by the microprocessor based on the stored signals and the current position of the plunger assembly.

11. The apparatus of claim 5, in which the plunger assembly further comprises diametrically opposite, axially extending slits in a sidewall of the plunger assembly, and in which the housing further comprises diametrically opposite, axially extending flanges protruding from an inner face of a sidewall of the housing and configured to mate with the axially extending slits of the plunger assembly.

* * * * *